US012567661B2

(12) United States Patent
Panhans et al.

(10) Patent No.: US 12,567,661 B2
(45) Date of Patent: Mar. 3, 2026

(54) ROTARY TRANSMISSION SYSTEM USING A WAVEGUIDE

(71) Applicant: Schleifring GmbH, Fürstenfeldbruck (DE)

(72) Inventors: Christian Panhans, Augsburg (DE); Reinhard Stolle, Aresing (DE)

(73) Assignee: Schleifring GmbH, Fürstenfeldbruck (DE)

( * ) Notice: Subject to any disclaimer, the term of this patent is extended or adjusted under 35 U.S.C. 154(b) by 103 days.

(21) Appl. No.: 18/385,608

(22) Filed: Oct. 31, 2023

(65) Prior Publication Data

US 2024/0063520 A1     Feb. 22, 2024

Related U.S. Application Data

(63) Continuation of application No. PCT/EP2022/055736, filed on Mar. 7, 2022.

(30) Foreign Application Priority Data

May 3, 2021    (EP) ...................................... 21171782
Sep. 1, 2021    (WO) ................. PCT/EP2021/074111
Jan. 14, 2022    (EP) ..................................... 22151542

(51) Int. Cl.
H01P 1/06        (2006.01)
A61B 6/00        (2024.01)
H01Q 13/06       (2006.01)
(52) U.S. Cl.
CPC ............... H01P 1/066 (2013.01); A61B 6/56 (2013.01); H01Q 13/06 (2013.01)

(58) Field of Classification Search
CPC .......... H01Q 21/24; H01Q 21/28; H01Q 3/08; H01Q 3/04; H01Q 1/38; H01Q 21/065;
(Continued)

(56) References Cited

U.S. PATENT DOCUMENTS

| | | | |
|---|---|---|---|
| 2,945,193 A | 7/1960 | Strom | |
| 5,530,422 A | 6/1996 | Harrison | |
| (Continued) | | | |

FOREIGN PATENT DOCUMENTS

| CN | 101552123 A | 10/2009 |
|---|---|---|
| EP | 0093468 B1 | 7/1987 |

OTHER PUBLICATIONS

Orfanidis, Chapter 9 Waveguides, in "Electromagnetic Waves and Antennas", Aug. 1, 2016, pp. 362-410.
(Continued)

*Primary Examiner* — Wei (Victor) Y Chan
(74) *Attorney, Agent, or Firm* — Quarles & Brady LLP; Yakov S. Sidorin

(57)                ABSTRACT

A coupler provides a high speed datalink between rotatable parts, which includes comprising a circular gap shaped as a hollow-cylindric volume and at least two antennae. The gap is formed between a first ring and a second ring rotatable against the first ring. A first antenna is mechanically coupled to the first ring and a second antenna is mechanically coupled to the second ring. The antennae are configured to effectuate a microwave signal connection between them the antennae based on multiple reflections of the signal at the rings.

19 Claims, 6 Drawing Sheets

(58) Field of Classification Search
CPC ........ H01Q 1/3275; H01Q 1/246; H01Q 1/32;
H01Q 9/0464; H01Q 21/062; H01Q
1/525
See application file for complete search history.

(56) References Cited

U.S. PATENT DOCUMENTS

| | | | | |
|---|---|---|---|---|
| 5,600,697 | A | 2/1997 | Harrison | |
| 5,646,962 | A | 7/1997 | Harrison | |
| 9,968,328 | B2 | 5/2018 | Murray | |
| 2007/0063785 | A1 | 3/2007 | Krumme et al. | |
| 2016/0235387 | A1* | 8/2016 | Murray | A61B 6/56 |
| 2017/0332991 | A1 | 11/2017 | Fackelmeier et al. | |
| 2019/0020121 | A1* | 1/2019 | Paulotto | H01Q 21/28 |
| 2019/0274578 | A1* | 9/2019 | Semenov | H01Q 13/10 |
| 2020/0194861 | A1 | 6/2020 | Vynohradov et al. | |
| 2020/0212528 | A1* | 7/2020 | Milroy | H01P 1/062 |

OTHER PUBLICATIONS

PCT International Search Report and Written Opinion, PCT/EP2022/055736, Jun. 27, 2022, 20 pages.

Song, H. et al., Terahertz Device Technologies for Ultrafast Data Downburst Applications, NTT Technical Review, 2015, 13(1):35-41.

European Patent Office, Extended Search Report, Application No. 25154679.2, Apr. 14, 2025, 13 pages.

European Patent Office, Extended Search Report, Application No. 21171782.2, Oct. 14, 2021, 10 pages.

CNIPA, Search Report, Application No. 2021800616670, Jun. 18, 2020, 7 pages.

CNIPA, Office Action, Application No. 2021800616670, Aug. 16, 2025, 7 pages.

* cited by examiner

ROTARY TRANSMISSION SYSTEM USING A WAVEGUIDE

CROSS-REFERENCE TO RELATED APPLICATIONS

This application is a continuation of the pending International Application No. PCT/EP2022/055736 filed on Mar. 7, 2022 and now published as WO 2022/233476, which designates the United States and claims priority from the European Patent Application No. 21171782.2 filed on May 3, 2021, International Patent Application No. PCT/EP2021/074111 filed on Sep. 1, 2021 and now published as WO/2022/053368, and the European Patent Application No. 22151542.2 filed on Jan. 14, 2022. The disclosure of each of the above-identified applications is incorporated by reference herein.

FIELD OF THE INVENTION

The invention relates to a rotary transmission system for providing a non-contact high speed datalink between rotatable devices and which may specifically be used for computed tomography scanners.

DESCRIPTION OF THE RELATED ART

Non-contact data links may be used to couple rotatable devices like the rotatable part of the gantry of a computed tomography (CT) scanner to the stationary part. Data rates are in the above 1 Gbit/s or even more than 10 Gbit/s range. Such data links may also be called a rotary joint or a slipring.

As CT scanners have a large inner bore for accommodation of a patient to be scanned, rotary joints used therein must have a large diameter, which normally is in the 1-1.5 m range. U.S. Pat. No. 5,646,962 discloses such a non-contact rotary joint which is based on a stripline for guiding a signal around a circular body and a capacitive pickup movable thereto for receiving said signal.

Another approach as disclosed in EP 0 093 468 uses a waveguide for transmitting signals. A stationary waveguide, comprising a circular shaped, conductive hollow body has a fixed receiving antenna. Further, a rotatable transmission antenna is movable in a radial slot in the body to couple signals into the interior of the waveguide. These signals travel along the waveguide until they reach the receiving antenna.

A problem is the comparatively small relative bandwidth of the waveguide, which limits the usable data rate. Further, the radial slot in the waveguide must be comparatively narrow to avoid degradation of the waveguide. The transmission antenna must fit into this slot and therefore can only be a small pin. Such an antenna is limited in its bandwidth and efficiency.

SUMMARY OF THE INVENTION

The problem to be solved by the invention is to provide improved high-speed coupling between rotatable parts.

Solutions of the problem are described in the independent claims. The dependent claims relate to further improvements of the invention.

A rotary joint which includes a high speed data link between rotatable parts also called a high speed data link rotary joint comprises a first ring and a second ring coaxially arranged around a center axis. The first ring has a first diameter and the second ring has a second diameter which is larger than the first diameter. The first ring and the second ring include at least partially conductive material. At least one ring may be of a metal e.g., copper, aluminum or steel. At least one ring may also have a conductive surface oriented to the other ring. The surface and/or the ring itself may also include a resistive and/or absorbing and/or attenuating material.

The first ring and the second ring have a circularly-shaped (in a cross-section) gap between them and thus may form a circularly-shaped (in a cross-section) channel. Further, the first ring and the second ring may be aligned axially. Basically, any of the rings may be stationary and/or rotatable. So, both rings may be stationary or both rings may be rotatable. Further one ring may be stationary while the other is rotatable.

The channel formed by the first and second rings (referred to below as simply channel) further may include at least one or two sidewalls. A first sidewall is located axially on one side of the rings, whereas the second sidewall is located axially on the other or opposing side of the rings. The first ring, the second ring, the first sidewall and the second sidewall form an enclosed channel which may have a rectangular or square cross-section. Basically, any of the sidewalls may be stationary, or rotatable.

The sidewalls are not necessary for the transmission function but can help to decouple the signal transmitted from the environment or neighboring channels by using reflective or absorptive sidewalls. Also the sidewalls may include a combination of absorbing material which may be mounted to a reflective surface. Thus, also a standard wireless network as e.g. IEEE 802.11 can be used without interfering with external wireless network installations used for other purposes.

For transmitting or coupling signals, a first antenna and a second antenna rotatable relative to the first antenna are provided. As both antennas are rotatable relative to each other, any antenna may be stationary where the other antenna is rotatable. The first and second antenna may rotate independent of any of the rings.

For coupling of RF signals, the first antenna may be directed into the circular gap, in a first direction, and under a first beam angle, herein further referred as first angle. The second antenna may be directed into the circular gap in a second direction opposing the first direction and under a second beam angle, herein further referred as second angle. The first angle and the second angle are defined relative to a radial direction of the center axis. They may have an absolute value in a range from 0° to 90° or a range between 1° to 89°. This allows to transfer microwave signals between the first antenna and the second antenna, if one of the antennas radiates signals into the gap and the other antenna receives signals from the gap. The first ring and the second ring may reflect microwave signals, such that the microwave signals propagate through the ring.

The first angle and the second angle may be fixed values, which do not change over rotation and therefore are constant over rotation. Further, the first antenna and the second antenna may have radiation patterns, which are constant over rotation.

In an embodiment, the first antenna may be mechanically coupled to the first ring and the second antenna is mechanically coupled to the second ring. The first antenna and the second antenna are directed into a space between the first ring and the second ring.

In an embodiment, an absolute value of the first angle may be larger than the width of the beam produced by the first antenna at a 3 dB level (a half-power level beam width of the first antenna) and an absolute value of the second angle may be larger than the 3 dB (half-power level) beam width of the second antenna. A simulation series and experimental evidence at specific data points has revealed that under these conditions the largest bandwidth with acceptable signal distortion can be achieved. Thus, dispersion caused by multiple paths may be kept at a level to allow for channel equalization with equalization techniques e.g. known form the IEEE 802.11 standards.

The rings and/or sidewalls may include an electromagnetically reflective material (that is, a material reflecting electromagnetic radiation) e.g. conductive material or may have a conductive surface or they may include a dielectric material with high permittivity. The conductive material of the rings may be of a higher conductivity metal e.g. aluminum or of a lesser conductive material e.g. steel. An absorptive material might be mounted to conductive or reflective surfaces to suppress multi-orbit signal propagation.

Such a rotary joint may be used in a gantry of a CT scanner which includes a stationary part and a rotatable disk, which rotates about a rotation axis. The rotatable disk may hold components like a power supply, an X-ray tube, an X-ray detector, and a data acquisition system. The rotary joint may receive data from the data acquisition system and couple these to the stationary part.

The gap may have a rectangular or square cross-section and may form a hollow cylindric volume. Therefore, it may be described as a hollow rectangular or square toroid. Normally, the gap may be a void space, filled with air, but it may also include a dielectric material, which may at least partially fill the gap. The circular gap may have a height corresponding to the radial distance between the first ring and the second ring and a width corresponding to the width of the rings, wherein the height and the width may be larger than two times the wavelength of the lowest frequency to be transmitted. If the rings have different widths, the width of the gap is determined by the smaller width.

In an embodiment, the first ring may be mounted and/or connected to the first sidewall, and the second ring may be mounted and/or connected to the second sidewall. This results in two parts which are rotatable against each other. There may be two sidewall-gaps between these two parts which may be very close or which may be bridged by sliding contacts, springs, a gasket or any other means which may provide low electrical impedance between these two parts, which may be a capacitive overlap. This improves shielding and avoids unwanted radiation. It is basically the same, if the first ring is mounted and/or connected to the second sidewall and the second ring is mounted and/or connected to the first sidewall.

In an embodiment, the first ring may be mounted to the first sidewall and to the second sidewall, such that the first ring is rotatable together with the first and second sidewalls. To allow a rotation, an axial or radial sidewall-gap may be provided on both sides of the second ring, such that the second ring can move freely against the first ring and the sidewalls. An inverted embodiment may include a second ring mounted to the first sidewall and the second sidewall.

Basically, there may be any combination of parts connected, as long as the first ring is rotatable against the second ring. Any sidewall-gap between rotatable parts may be bridged by sliding contacts, springs, a gasket or any other means which may provide low electrical impedance between these two parts, which may be a capacitive overlap. The sidewall-gap may have a width of 0.5 to 4 mm, which may be just big enough to allow rotation and mechanical tolerances of objects of that size.

In an embodiment, the first ring and the second ring may have the same width and are axially aligned. Further, the first sidewall and the second sidewall may be flat disk-shaped rings covering the space between the first ring and the second ring. At least one of the sidewalls may overlap at least one of the rings to bridge a sidewall-gap there-between and to provide at least a capacitive coupling. The overlap might be dimensioned to be a quarter or multiple quarters of the wavelength.

In an embodiment, the distance between the first ring and the second ring is one of: equal or less than two times the wavelength of a signal to be transmitted, equal or less than five times the wavelength. The distance may be five times the wavelength with a tolerance of plus or minus 50%. This may allow for lowest dispersion between the signal paths with lowest and highest number of reflections.

In an embodiment, the first antenna and/or the second antenna have an adjustable directivity wherein transmitted power and receiver sensitivity together with conductivity of the reflective surface of inner and second ring may be configured for a predetermined number of reflections between the rings leading to a sufficiently low signal after one round of propagation.

In an embodiment, the first antenna and/or the second antenna are directed into the circular gap. If a microwave signal is radiated into the gap, it will be reflected by the rings, such that it can be received from the gap. Therefore, in general the embodiments may work with unspecific antennas simply radiating into the gap and receiving from the gap. Improved transmission may be achieved by directing the first antenna under a first angle towards the second ring and the second antenna under a second angle towards the first ring. This ensures proper reflection by the rings to transfer the signals which may be alternatingly reflected by the first and second ring. In a further embodiment, the antennas may have a configurable directivity. This means that they have an adjustable radiation pattern. This may simply be achieved by phased array antennas. The radiation pattern may be adjusted such that a specific angle of reflection is obtained which may result in a well-defined signal path between the first antenna and the second antenna. There may also be different or multiple signal paths. Too many different signal paths may have negative effects if the dispersion caused by differences in the propagation time of the paths—the delay spread—is too large to be compensated by e.g. an equalizer. This may decrease transmission rate and/or transmission quality. In an example, there may be a first signal path having two reflections, and another signal path having four reflections.

In an embodiment, at least one of the first antenna and the second antenna may be mounted flush to a surface of at least one of the first ring and the second ring. Alternatively, they may be mounted within the gap. They may be mounted on different radii and/or displaced in the direction of rotation axis. They may be mounted on a support structure outside the gap 250.

In an embodiment, a main beam of the at least one antenna may be diverted electronically or by reflector. Such an adjustment may be made before a rotation, and during rotation, the adjustment may be kept without change.

In an embodiment, the first antenna and the second antenna may be configured for a microwave or millimeter wave signal connection.

Another embodiment relates to a data link between movable parts comprising a hollow gap in general. This hollow gap may have a linear shape, but it may also have any other shape like a combination of linear and/or curved sections.

The hollow gap may include four sidewalls which may define a rectangular or squared cross-section. This embodiment is comparable to the circular gap embodiments disclosed herein. The linear hollow gap may include a first sidewall with a first antenna, and a second sidewall opposing thereto with a second antenna. The first and second sidewalls may be parallel to each other to allow reflections between the first and second sidewalls. There may be third and fourth sidewalls at the sides of the first and second sidewalls to form the hollow gap.

The circular gap may have a height and a width. Also, the linear hollow gap may have a height and a width. The gap can only guide microwave signals if a wavelength of the microwave signal is shorter than 2 times the width or the height, whichever is larger. The embodiments work best, if at least one wavelength of the microwave signals, which may have multiple different wavelengths, is shorter than $\frac{1}{2}$, $\frac{1}{3}$, $\frac{1}{4}$, $\frac{1}{5}$, or $\frac{1}{10}$, or $\frac{1}{20}$ or $\frac{1}{50}$, or $\frac{1}{100}$ of the width or the height, whichever is larger. The smaller the wavelength of the signal is compared to the width or to the height of the gap, the more transmission paths under different angles are possible. As the microwave signal may be reflected between the first and the second ring, or between the first and second sidewalls, at least one wavelength of the microwave signal may be shorter than $\frac{1}{2}$, $\frac{1}{3}$, $\frac{1}{4}$, $\frac{1}{5}$, or $\frac{1}{10}$, or $\frac{1}{20}$ or $\frac{1}{50}$, or $\frac{1}{100}$ of this distance.

The distance between the first ring and the second ring may be significantly larger than half of a wavelength of the transmitted signal to allow for a multimode propagation of the signal.

Herein, the term microwave is used for radiofrequency signals which are in a range of more than 300 MHz. In an embodiment, signals in a range above 2 GHz may be used. Very good transmission characteristics have been obtained with signals in a 60 GHz range. The embodiments may also use frequencies of several 100 GHz or more.

In an embodiment, the data transmission implemented may conform to a wireless standard e.g. IEEE802.11 ad or ay.

The dimensions of inner and second ring may be optimized to achieve a typical number of reflections when the microwave signal is propagating one round. The strategy to optimize the beam angle may be to find an angle based on a defined antenna directivity, which may result in a transmitted narrow beam of high amplitude with a strong attenuation outside the beam and few side lobes. The same directivity profile may be present at the receive side. Also, the beam angle may not be too close to 0° to avoid that the reflections at the opposing ring go back into the antenna. This may be achieved with a two-dimensional patch antenna as phased array antenna with sufficient angular resolution.

In an alternate embodiment, at least one of the first antenna and the second antenna may include a phased array antenna and/or a horn antenna, wherein the at least one antenna may have a directivity of at least 5 dBi Also, the reflection attenuation defined by conductivity and angle of reflection may be optimized, a higher conductivity of the material leads to a lower attenuation, a lower conductivity to a higher attenuation. The strategy is to reduce dispersion (delay spread) between signals having a different number of reflections because of the higher attenuation caused with every reflection.

One angle of reflection may be defined by the directivity characteristic of the main beam of the antenna with highest gain and side lobes may be present but experience a higher reflection attenuation that additionally attenuates these paths so that e.g. with a narrow 3 dB beam width of the antenna, for each position, the majority of the signal paths varies only slightly in regard to its total path lengths and angles.

Another method to reduce dispersion (delay spread) is to allow only a portion of the propagable paths between both antennas. This may be achieved by using an antenna with small 3 dB beam width, an antenna with high directivity which may reduce the number of paths. Paths that have an angle close to the beam angle have small path length differences and transmit most of the energy because they experience high antenna gain. Other paths outside the main beam, e.g. in the area of the side lobes, may be too attenuated to affect the transmission significantly. The wider the beam width may be chosen and the larger the rotation angle may be, the more paths may fall into the beam width, e.g. 3-dB beam width, and the larger may be the occurring dispersion. The beam width may therefore be selected to be narrow enough so that the dispersion may be small enough for a full rotation at a rotation angle of 360°.

Axial displacement of transmitter and receiver may reduce the dynamic range of received signal strengths between minimum signal path 0 degrees and signal path 360 degrees.

At rotation angles close to 0°, where the first antenna and the second antenna are proximate to each other, the attenuation of the signal may be minimal. The range between the attenuation that occurs at this angle of rotation and the maximum possible attenuation during a full rotation determines the dynamic range requirement of the transmission system. To keep this value as low as possible, the antennas can be axially displaced to increase the path length for this rotation angle range and to achieve propagation paths between the two antennas that run at the edge or outside the main beam.

An embodiment may use a feature of the wireless standards as e.g. IEEE802.11 ad or ay: the guard interval together with OFDM or single carrier with frequency domain equalization. The transceiver may periodically train on the characteristics of the gap. Multiple transmission paths like clockwise and counterclockwise transmission can be employed. A guard interval of the standard applied may be selected such that it is longer than the total signal propagation time through the gap covering a full orbit (360 degrees) of the rotary joints gap. For a given guard interval and a given minimum diameter of the first ring, the distance between the first ring and the second ring may be adapted to obtain a predetermined maximum path length resulting in a predetermined maximum signal propagation time.

Guard intervals of the above-mentioned wireless standards may be used to allow for dispersion caused by multi-path propagation and dispersion caused by one or more orbits. There may be a training to optimize the guard intervals.

Attenuating material may be mounted to at least one of the rings axially to the antenna and in the vicinity of the antenna to attenuate a part of the signal that propagates more than a full round, reducing the interference of directly received signal and signal that propagates more than one round.

There might be several parallel gaps arranged radially or axially. The axial arrangement is preferred with multiple antennas having sidewalls to separate gaps. Thus, the total transmission capacity can be increased when there is sufficient attenuation between the gaps.

In an embodiment, the first antenna may be electrically coupled to a transmitter and the second antenna may be electrically coupled to a receiver. In another embodiment, the first antenna may be electrically coupled to a receiver and the second antenna may be electrically coupled to a transmitter. In a further embodiment, the first antenna may be electrically coupled to a first transceiver and the second antenna may be electrically coupled to a second transceiver. The transmit and receive frequencies might be different at a transceiver to have a better signal separation between the communication channels.

In an embodiment, a rotary joint may have a first component and a second component, wherein the first component may be rotatable relative to the second component. The first antenna may be at the first component and the second antenna may be at the second component. The first ring and the second ring may be at either component.

BRIEF DESCRIPTION OF THE DRAWINGS

In the following the invention will be described by way of example, without limitation of the general inventive concept, on examples of embodiment with reference to the drawings.

DETAILED DESCRIPTION

Figure 1:
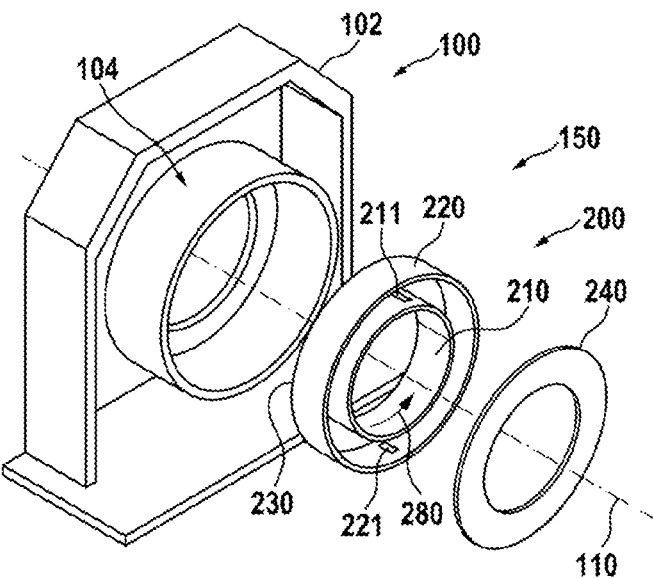
FIG. 1 shows an embodiment.

In FIG. 1, the first embodiment is shown. A gantry 100 of a CT scanner comprises a stationary part 102 and a rotatable part 150 including rotatable disk 104, rotatable about a rotation axis 110. The rotatable disk may hold rotatable components which are not shown here, like a power supply, an X-ray tube, an X-ray detector and a data acquisition system. Further, a slip ring or a rotatable power transformer which is also not shown, may be provided for transfer of power from the stationary to the rotatable part.

The rotatable part 150 may include a rotary joint 200 for high speed data transmission. The rotary joint 200 may include a first ring 210 and a second ring 220, both rings may be on the same axis. The embodiment would also work with offset axes. Both rings may be rotatable against each other. Any one of the rings may be stationary, whereas the other may be rotatable.

Further, a first sidewall 230 and/or a second sidewall 240 may be provided. Also, at least one of the sidewalls may be part of a gantry 100 of a CT scanner. Each sidewall may be fixed to one of the rings 210, 220. There may also be a low impedance contact between a sidewall and a ring. To the other ring there may be a sidewall-gap, which may be bridged by sliding brushes, a conductive gasket or any other suitable material which may provide a good electrical contact.

In an embodiment, the ring 210 and both sidewalls 230, 240 may be connected together forming a U-shaped cross section, while ring 220 is rotatable. There may be sidewall-gaps at the sides of the second ring 220 to allow for rotation. There may be any other combination of connected parts which may allow rotation of the rings 210 and 220 with their mechanically coupled antennas 211 and 221 and may form a toroid with rectangular section together with sidewalls.

Both rings 210, 220 may have the same width and may be axially aligned. The sidewalls 230, 240 may be flat disk shaped rings, they may also overlap at least one of the first ring 210 and the second ring 220.

The rings 210, 220 and the sidewalls 230, 240 comprise an electrically conductive material like a metal and or a material with electrically conductive surfaces.

A first antenna 211 is rotatable against a second antenna 221. Both antennas are directed into the volume between the rings. The antennas may rotate or be stationary with their rings, the antennas may be mounted to the rings.

Figure 2:
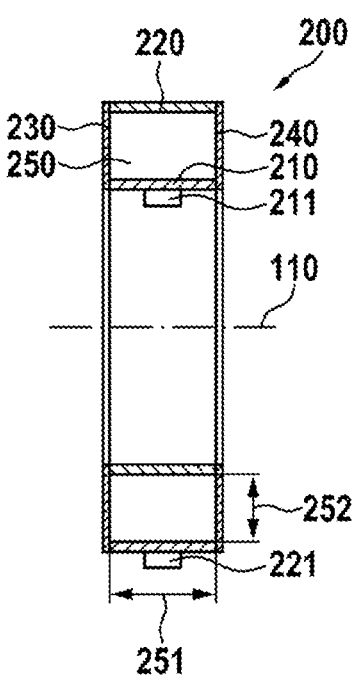
FIG. 2 shows a sectional side view of the circular gap.

FIG. 2 shows a sectional side view of an embodiment of the rotary joint 200 having sidewalls. The rotary joint may have a rectangular or squared cross section with a width 251 between the sidewalls 230, 240 and a height 252 between the rings 210, 220.

The rotary joint 200 has an inner space which allows the propagation of electromagnetic waves with a maximum wavelength Amax equals to two times the width 251 or the height 252, whichever is larger.

Since the sidewalls 230, 240 are not necessary for the function they can be omitted, then the width of the gap may be the smallest width of the rings 210, 220. Such an embodiment is shown in FIG. 3.

Figure 3:
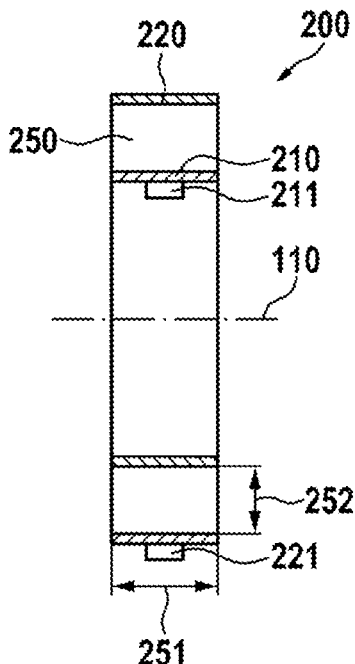
FIG. 3 shows a sectional side view without sidewalls.

FIG. 3 shows a similar sectional side view as the previous figure, but without sidewalls 230, 240. Here, some radiation energy may be lost through the open sides, but still a significant part of radiation remains guided between the rings.

Figure 4:
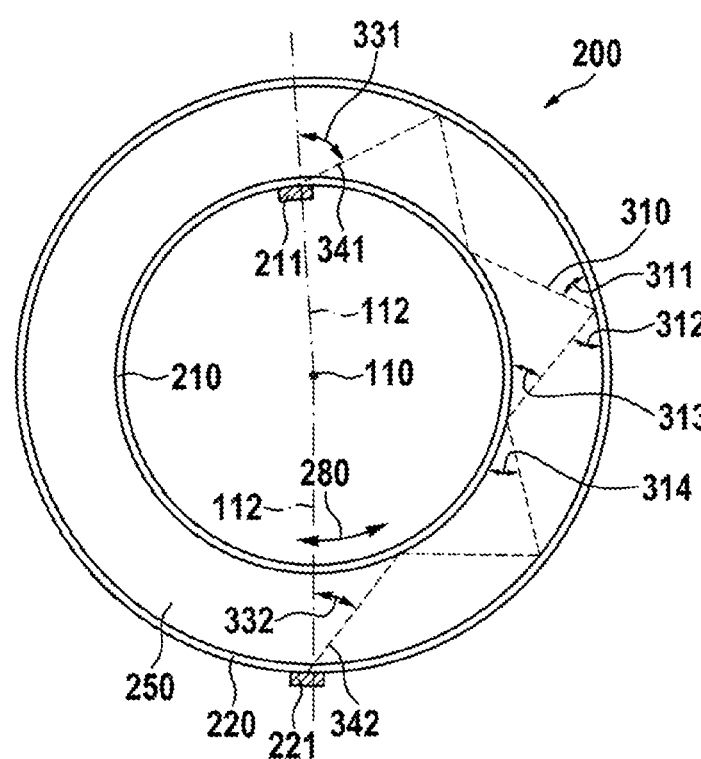
FIG. 4 shows a front view into the circular gap.

FIG. 4 shows a front view into the circular gap 250 with a possible signal path between first antenna 211 and outer antenna 221. The signal may not only be transmitted in a single mode within the circular gap 250, but it may also be reflected at the first ring 210 and or the second ring 220. In this figure, first antenna 211 and outer antenna 221 may have a relative angle (angle of rotation) of about 180 degrees. The first antenna 211 may emit a signal with a first beam 341 under an angle 331 to a radial direction 112. Here, a radial direction is on a line 112 going under a right angle through rotation axis 110. There may be multiple reflections at the rings as shown and dependent of the specific direction of radiation of the antennas. With each reflection the angles of the electromagnetic wave 310 to be reflected and the reflected wave versus a surface of a ring are the same. Such, the first reflection angle at second ring 311 is the same as the second reflection angle at second ring 312 and the first reflection angle at first ring 313 is the same as second reflection angle at first ring 314. The second antenna 221 may receive the signal with a second beam 342 under an angle 332 to a radial direction 112. Here, the sum of reflection angles 311 (or 312) and 332 may be 90°, as well as the sum of reflection angles 313 (or 314) and 331. Here, the beam is only indicated by its centerline. In addition to the beam angle which is the angle of maximum radiation level, the antenna beam may be also characterized by the 3 dB or half power beam width. The half power beam width is the angular width (in degrees), of the major beam or lobe of an antenna radiation pattern at which the signal power is half that of its peak value. As antennas are reciprocal, transmit and receive function may be exchanged. Here, the first antenna 211 and second antenna 221 may be at the first ring 210 and the second ring 220. They may be attached at the ring and radiate through a hole in the ring.

Figure 5:
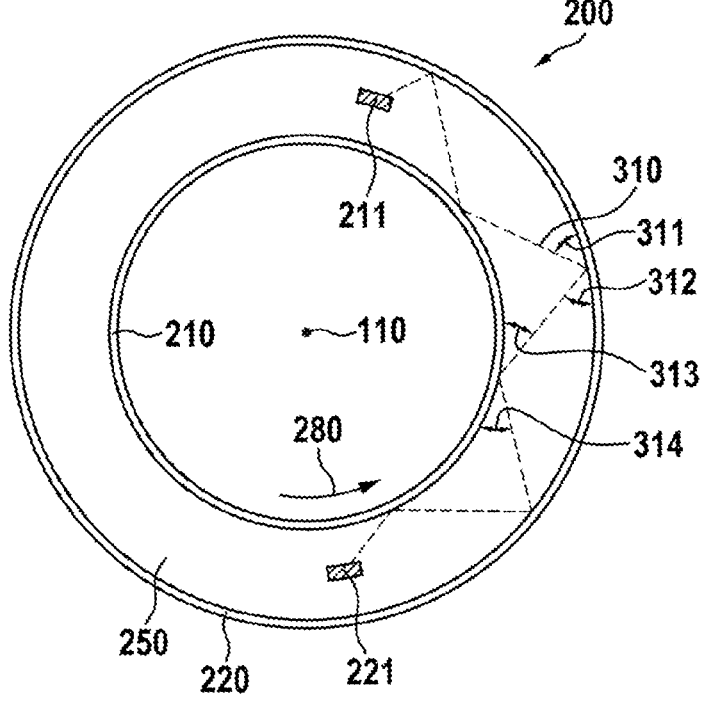
FIG. 5 shows an embodiment with antennas within the gap.

FIG. 5 shows a similar embodiment as in the previous figure. Here first antenna 211 and second antenna 221 are within the gap 250. They may be mounted on different radii and/or displaced in the direction of rotation axis 110. They may be mounted on a support structure outside the gap 250.

Figure 6:
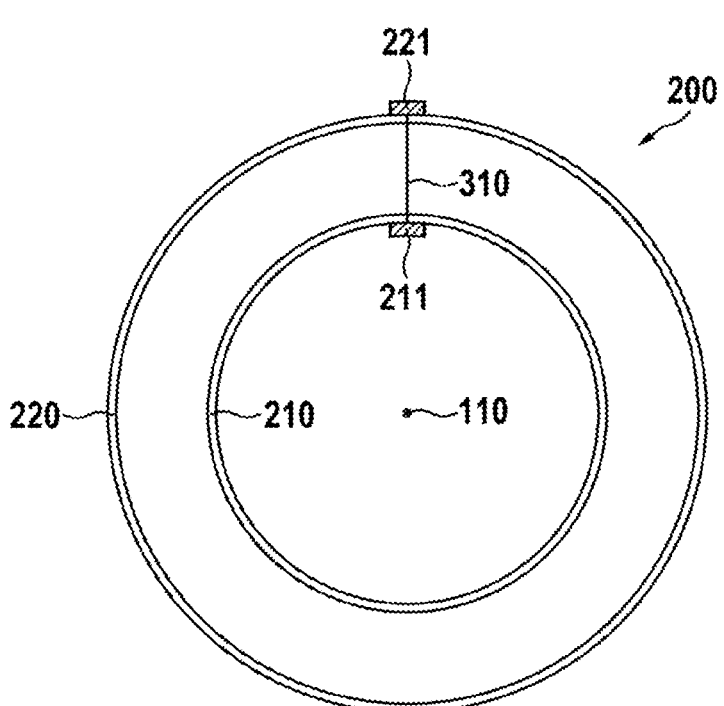
FIG. 6 shows a further front view into the circular gap.

FIG. 6 shows a further front view of the rotary joint 200 into the circular gap 250 between first ring 210 and second ring 220. In this figure, first antenna 211 and second antenna 221 have a relative angle of about 0 degrees, such that they are opposing each other. Here, the electromagnetic wave 310 may directly propagate from first antenna 211 to second antenna 221. During rotation the relative angles between the antennas is constantly changing, the 0 degree position shown here and also other relative angles shown in the other figures are present only for a short time.

Figure 7:
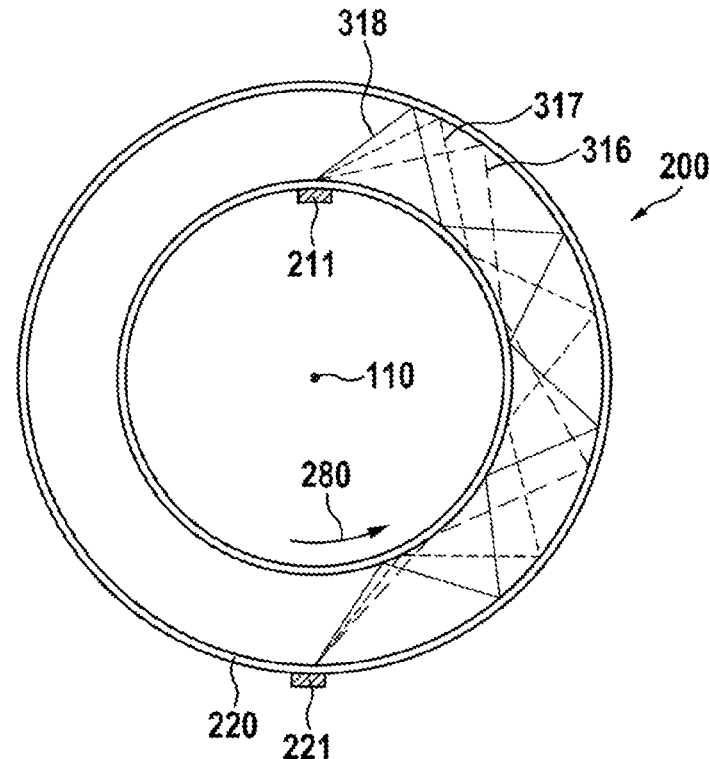
FIG. 7 shows a multipath propagation.

FIG. 7 shows a multipath propagation. In this figure, first antenna 211 and second antenna 221 have a relative angle of about 180 degrees. Here three different multipath propagations 316, 317, 318 are shown. With a small 3 dB beam width the antennas help to minimize dispersion caused by the multiple paths having different propagation times by attenuating paths with even longer or shorter propagation lengths.

Figure 8:
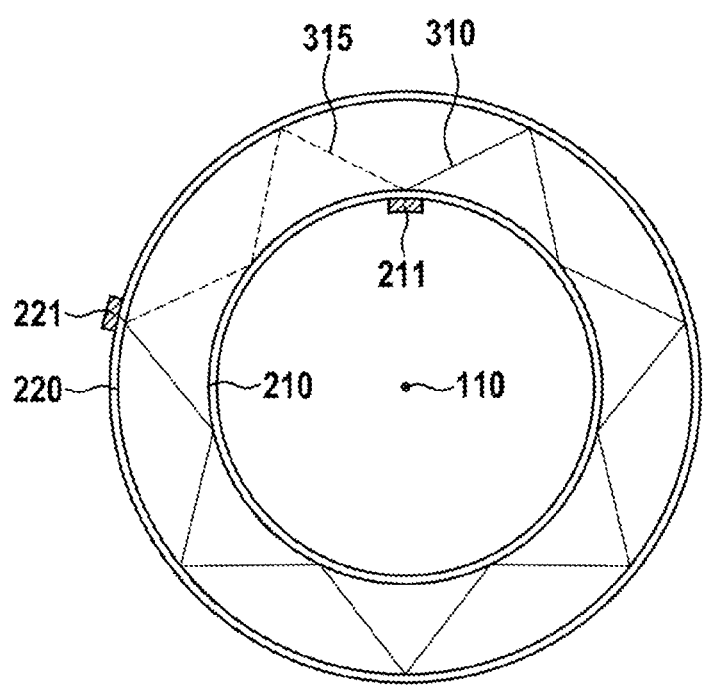
FIG. 8 shows a dual path propagation.

FIG. 8 shows an embodiment having a dual path propagation. In this figure, first antenna 211 and second antenna 221 have a relative angle of about 270 degrees. Here, the electromagnetic wave 310 may propagate clockwise from first antenna 211 to second antenna 221. There may also be a second counterclockwise signal path 315, if the antenna gain at the given beam angles is high enough and the attenuation by the reflections is low enough, the anticlockwise path may contribute to the receive signal. To enable the equalizer of the receiver to compensate the effects caused by the addition of the two signals the guard interval may cover at least one propagation time around the 360 degrees of the rotary joint. The signal along both paths are alternatingly reflected by the first and second ring. Further, both signal paths may be used for bidirectional signal transmission. This example shows a relative angle of about 270 degrees, but two signal paths are basically available through all relative angles between first antenna 211 and second antenna 221.

Figure 9:
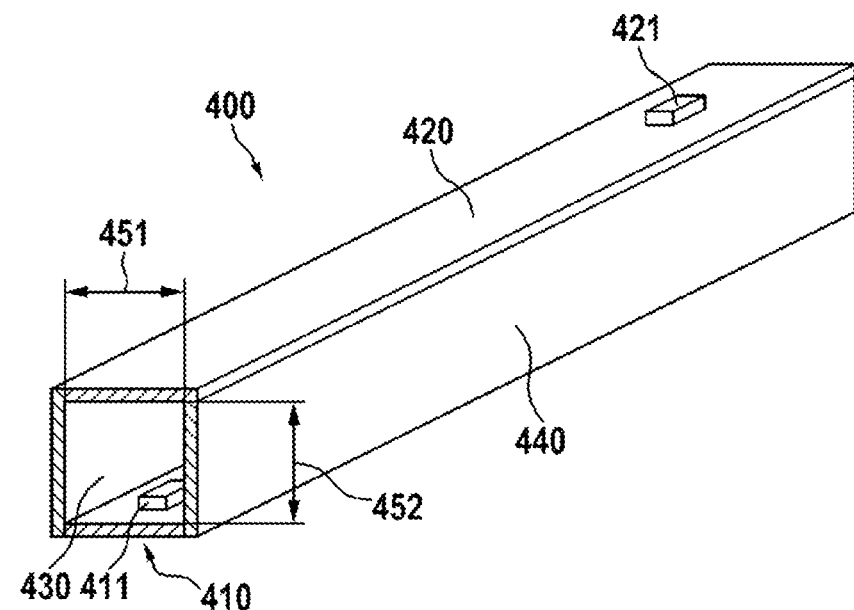
FIG. 9 shows a linear embodiment.

FIG. 9 shows a linear embodiment. A hollow gap 400 includes four sidewalls 410, 420, 430, 440, defining a rectangular cross sectioned or square cross sectioned hollow space. A first sidewall 410 is parallel to a second sidewall 420. Further, a first antenna 411 is mechanically coupled to the first sidewall 410 and a second antenna 421 is movable within the linear gap. The second antenna may be mechanically coupled to the second sidewall. The sidewalls 410, 420, 430, 440 include an electrically conductive material like a metal. They may be made from such a material or they may have a conductive surface which may include such a material. The first antenna 411 and the second antenna 421 are configured for a microwave signal connection 169 between them. This embodiment is basically the same as the circular embodiments disclosed herein, but is linear. The first sidewall 410 corresponds to the first ring 210 and the second sidewall 420 corresponds to the second ring 220. Further, an embodiment may have any shape like a combination of curved sections and/or linear sections.

Figure 10:
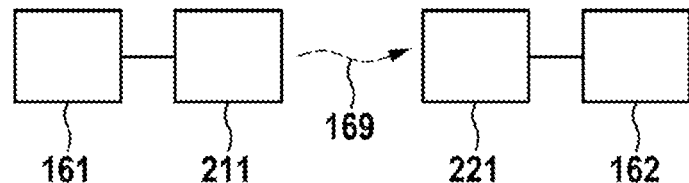
FIG. 10 shows an exemplary functional block diagram.

FIG. 10 shows an exemplary functional block diagram. A transmitter 161, which may be fed by a data acquisition system providing imaging data sends signals to first antenna 211 which radiates microwave signals 169 into the circular gap 250. These RF signals 169 are received by antenna 221 and forwarded to a receiver 162. Basically, the direction may be reversed. Also a bidirectional communication may be made.

Figure 11:
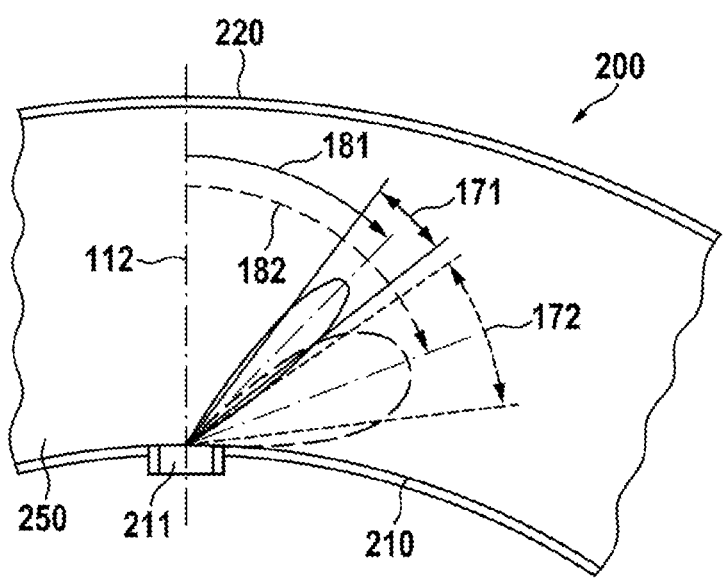
FIG. 11 shows an exemplary relation of beam with and beam angle.

FIG. 11 shows an exemplary relation of beam with and beam angle. The larger the beam angle is, the larger the beam width that can be set. This relation limits the dispersion caused by multi-path delay spread. The relation is valid for a first antenna shown here, but also applies to a second antenna. Here a first antenna 211 has a first beam width 171 (3 dB width) and a first beam angle 181. In a case, the first antenna has a second beam width 172 which is larger than the first beam width, then the corresponding second beam angle 182 would be larger than the first beam angle 172. Both beam width are defined as 3 dB (half power) beam widths.

LIST OF REFERENCE NUMERALS

100 gantry of CT scanner
102 stationary part
104 rotatable disk
110 rotation axis
112 radial direction
150 rotatable part
161 transmitter
162 receiver
169 RF signals
171 first beam width
172 second beam width
181 first beam angle
182 second beam angle
200 rotary joint
210 first ring
211 first antenna
220 second ring
221 second antenna
230 first sidewall
240 second sidewall
250 gap
251 width
252 height
310 electromagnetic wave propagation
311 first reflection angle at second ring
312 second reflection angle at second ring
313 first reflection angle at first ring
314 second reflection angle at first ring
315 alternate electromagnetic wave propagation
316 first multipath propagation
317 second multipath propagation
318 third multipath propagation
331 first beam angle
332 second beam angle
341 first beam
342 second beam
400 hollow gap
410 first sidewall
420 second sidewall
411 first antenna
420 second sidewall
421 second antenna
430 third sidewall
440 fourth sidewall
451 width
452 height

What is claimed is:
1. A high speed datalink rotary joint comprising:
a first ring with a first diameter and a second ring with a
second diameter that is larger than the first diameter, the first ring being coaxially arranged to the second ring and around a center axis to form a gap between the rings, the first ring and the second ring comprising at least partially conductive material, the rotary joint further comprising a first antenna and a second antenna rotatable relative to the first antenna, the first antenna being directed into the gap in a first direction and at a first angle, the second antenna being directed into the gap in a second direction opposing the first direction and at a second angle, and wherein each of the first angle and the second angle is defined relative to a radial direction of the center axis and has an absolute value in a range from 0° to 90°, wherein each of values of the first angle and the second angle is a fixed value and remains over rotation, wherein an absolute value of the first angle is larger than a width of a beam of the first antenna measured at a half-power level and/or an absolute value of the second angle is larger than a width of a beam of the second antenna measured at a half-power level.

2. The high speed datalink rotary joint according to claim 1, wherein no sidewalls are provided between the first ring and the second ring.

3. The high speed datalink rotary joint according to claim 1, wherein the gap has a rectangular cross section.

4. The high speed datalink rotary joint according to claim 1, wherein the gap has a width and a height that corresponds to a radial distance between the first ring and the second ring, wherein each of the height and the width is larger than two times a wavelength of a signal having the lowest frequency of signals to be transmitted by the first antenna and/or the second antenna.

5. The high speed datalink rotary joint according to claim 1, wherein an absolute value of the first angle is equal to an absolute value of the second angle.

6. The high speed datalink rotary joint according to claim 1, wherein the first antenna and the second antenna are axially displaced from one another.

7. The high speed datalink rotary joint according to claim 1, wherein the first antenna is mechanically coupled to the first ring and/or the second antenna is mechanically coupled to the second ring.

8. The high speed datalink rotary joint according to claim 1, wherein each of the first antenna and the second antenna has a corresponding radiation pattern that is constant over rotation.

9. The rotary joint according to claim 1, wherein each of the first antenna and the second antenna is configured for a microwave or millimeter wave signal connection.

10. The high speed datalink rotary joint according to claim 1, wherein the first antenna is electrically coupled to a transmitter and the second antenna is electrically coupled to a receiver, or the first antenna is electrically coupled to the receiver and the second antenna is electrically coupled to the transmitter, or the first antenna is electrically coupled to a first transceiver and the second antenna is electrically coupled to a second transceiver.

11. The high speed datalink rotary joint according to claim 1, wherein at least one of the first antenna and the second antenna includes a phased array and/or a horn antenna.

12. The high speed datalink rotary joint according to claim 10, wherein each of the transmitter, the receiver, and the first and second transceivers is configured for OFDM or single carrier with frequency domain equalization.

13. The high speed datalink rotary joint according to claim 1, wherein at least one of the first antenna and the second antenna is mounted flush to a surface of at least one of the first ring and the second ring.

14. The high speed datalink rotary joint according to claim 1, wherein-at least one of the first and second rings includes an electromagnetically reflective material or includes a dielectric material with high permittivity.

15. The high speed datalink rotary joint according to claim 3, wherein the gap has a hollow cylindrical volume.

16. The high speed datalink rotary joint according to claim 9, wherein the first ring and the second ring are configured to alternatively reflect the microwave or millimeter wave signal.

17. The high speed datalink rotary joint according to claim 11, wherein the at least of the first antenna and the second antenna has a directivity of at least 5 dBi.

18. The high speed datalink rotary joint according to claim 13, configured to divert a main beam of the at least one of the first antenna and the second antenna electronically or with a reflector.

19. The high speed datalink rotary joint according to claim 14, wherein the electromagnetically reflective material includes an electrically conducting material.

* * * * *